(12) United States Patent
Li et al.

(10) Patent No.: US 6,836,529 B2
(45) Date of Patent: Dec. 28, 2004

(54) METHOD AND APPARATUS OF CT IMAGING WITH VOLTAGE MODULATION

(75) Inventors: Jianying Li, New Berlin, WI (US); Steven J. Woloschek, Franklin, WI (US); Thomas L. Toth, Brookfield, WI (US); Jonathan R. Schmidt, Wales, WI (US)

(73) Assignee: General Electric Company, Milwaukee, WI (US)

( * ) Notice: Subject to any disclaimer, the term of this patent is extended or adjusted under 35 U.S.C. 154(b) by 0 days.

(21) Appl. No.: 09/683,781

(22) Filed: Feb. 13, 2002

(65) Prior Publication Data

US 2003/0152189 A1 Aug. 14, 2003

(51) Int. Cl.[7] .............................................. G01N 23/00
(52) U.S. Cl. ......................................... 378/8; 378/111
(58) Field of Search ................................ 378/108, 113, 378/8, 16, 109, 111, 95

(56) References Cited

U.S. PATENT DOCUMENTS

| | | | |
|---|---|---|---|
| 5,301,108 A | 4/1994 | Hsieh | |
| 5,751,782 A | 5/1998 | Yoshitome | |
| 6,275,560 B1 * | 8/2001 | Blake et al. | 378/8 |
| 6,298,111 B1 * | 10/2001 | Ozaki | 378/8 |
| 6,298,117 B1 * | 10/2001 | Hampel et al. | 378/150 |
| 6,560,309 B1 * | 5/2003 | Becker et al. | 378/8 |

FOREIGN PATENT DOCUMENTS

| | | |
|---|---|---|
| EP | 1 013 225 A1 | 6/2000 |
| WO | WO 01/043642 A3 | 6/2001 |

* cited by examiner

*Primary Examiner*—David V. Bruce
*Assistant Examiner*—Hoon Song
(74) *Attorney, Agent, or Firm*—Ziolkowski Patent Solutions Group, LLC; Michael A. Della Penna; Carl B. Horton

(57) ABSTRACT

A system and method of diagnostic imaging with reduced x-ray exposure to the scan subject during scanning includes acquiring a set of cardiac signals or other motion (cardiac mechanical motion or respiratory motion) related signals and determining and imaging profile therefrom. Pursuant to the imaging profile, voltage applied to an x-ray source is modulated to provide an energizing voltage during primary data acquisition stages and a reduced voltage during secondary or non-data acquisition stages. Voltage modulation repeats until sufficient data for image reconstruction has been acquired.

20 Claims, 4 Drawing Sheets

METHOD AND APPARATUS OF CT IMAGING WITH VOLTAGE MODULATION

BACKGROUND OF THE INVENTION

The present invention relates generally to diagnostic imaging and, more particularly, to a method and apparatus of acquiring diagnostic imaging data with voltage modulation to reduce radiation exposure.

Typically, in computed tomography (CT) imaging systems, an x-ray source emits a fan-shaped beam toward an object, such as a patient. The beam, after being attenuated by the scan subject, impinges upon an array of radiation detectors. The intensity of the attenuated beam radiation received at the detector array is typically dependent upon the attenuation of the x-ray beam by the patient. Each detector element of the detector array produces a separate electrical signal indicative of the attenuated beam received by each detector element. The electrical signals are transmitted to a data processing for subsequent image reconstruction.

Reducing radiation exposure during a CT scan has always been a desired goal and is becoming increasingly important with the introduction of multi-slice CT scanning for patient screening, such as coronary artery calcification scoring (CACS) tests and coronary artery imaging (CAI). For CACS tests, known multi-slice CT scanning systems often use step-and-shoot scanning and EKG-based prospective gating techniques to eliminate radiation redundancy. That is, the x-ray source is on for only a certain period during the heart cycle to emit radiation toward the scan subject and thereby allow acquisition of the data necessary for "step-and-shoot" scanning. To provide adequate coverage within a patient breath holding time in accordance with a "step-and-shoot" scan, it is customary to use a relatively thick slice (for example, a slice thickness of 2.5 mm).

It is often desirable to use thinner slice thicknesses to improve image quality and to use continuous patient feeding (helical scans) to improve coverage and patient throughput without introducing redundant exposure during CACS tests. This requires turning on the x-rays for the cardiac period when the heart has the least motion and turning off the x-rays for the remainder of the heart cycle during a single, long helical scan.

It is also customary in coronary artery imaging for helical scanning and thin slice collimation (1.25 mm) to be used to provide good image quality and adequate coverage. Patients are continuously fed along the patient long-axis while the x-ray is on to provide continuous volume coverage and full cardiac cycle imaging. However, it has been realized that not all cardiac phases in a cardiac cycle are equally important. Full image quality should be provided for those cardiac phases when heart has the least motion. While images are needed for other phases when the heart has greater motion to provide a complete picture for the coronary artery imaging tasks, image quality may be compromised.

Another method to achieve these scanning modes is to reduce patient exposure to x-rays include modulating an x-ray tube current based on the cardiac cycle. This method has certain drawbacks, however, since the cooling time of the filament in the x-ray tube limits the modulation response resulting in increased patient exposure to x-rays. Additionally, the x-ray tube requires a minimum current in order to operate.

Therefore, it would be desirable to design an apparatus and method for acquiring data for image reconstruction without unnecessary radiation exposure to the scan subject in completing the CACS tasks and with reduced radiation exposure to the scan subject in completing the CAI tasks. It would be further desirable to design such a system without sacrificing image quality or subject throughout.

BRIEF DESCRIPTION OF THE INVENTION

The present invention is a directed method and apparatus for acquiring imaging data with voltage modulation to reduce radiation exposure to the scan subject that overcomes the aforementioned drawbacks.

Therefore, in accordance with one aspect of the present invention, a method of voltage modulation for computed tomography (CT) imaging is provided. The method includes the steps of acquiring a set of EKG signals having a plurality of triggering pulses and determining a period of delay after each triggering pulse. The method further includes the step of energizing a high frequency electromagnetic energy source to a first voltage after each period of delay and acquiring a set of imaging data of a scan subject while the high frequency electromagnetic energy source is energized to the first voltage. After acquiring a set of imaging data, the high frequency electromagnetic energy source is then energized to a second voltage until a period of delay after a next triggering pulse.

In accordance with another aspect of the present invention, a radiation emitting imaging system includes a high frequency electromagnetic energy projection source configured to project high frequency energy toward a scan subject. The system also includes a detector assembly configured to receive high frequency electromagnetic energy attenuated by the scan subject and output a plurality of electrical signals indicative of the attenuation to a data acquisition system. The system further includes a control configured to determine a plurality of primary data acquisition stages and a plurality of secondary acquisition stages. The control is further configured to energize the high frequency electromagnetic energy projection source to a first voltage during each data acquisition stage to acquire imaging data. The control is also configured to energize the high frequency electromagnetic energy projection source to a second voltage during each secondary acquisition stage. The control is also configured to reconstruct an image of a scan subject from the imaging data acquired during each data acquisition stage.

In accordance with a further aspect of the present invention, a computer readable storage medium having a computer program stored thereon and representing a set of instructions is provided. The set of instructions when executed by a computer causes the computer to analyze a set of cardiac motion signals acquired from a set of sensors affixed to a torso region of a scan subject. The set of instructions further causes the computer to determine from the set of cardiac motion signals a number of primary data acquisition stages and a number of secondary acquisition stages. The computer is then caused to transmit a first voltage modulation signal to a voltage source configured to energize an x-ray projection source used to project x-rays to the scan subject for data acquisition. The first voltage modulation signal is configured to drive the voltage source to the first voltage during each data acquisition stage. The computer is then caused to acquire a set of imaging data. Thereafter, the computer is caused to transmit a second voltage modulation signal to the voltage source wherein the second voltage modulation signal is configured to drive the voltage source to a second voltage for each secondary acquisition stage.

Various other features, objects and advantages of the present invention will be made apparent from the following detailed description and the drawings.

BRIEF DESCRIPTION OF THE DRAWINGS

The drawings illustrate one preferred embodiment presently contemplated for carrying out the invention.

In the drawings.

DETAILED DESCRIPTION

The present invention is direct to a system and method for acquiring imaging data of a scan subject using voltage modulation to reduce x-ray exposure to the scan subject. The present invention will be described with respect to a computed tomography system, but one skilled in the art will readily appreciate that the present invention is also applicable to other radiation emitting imaging systems. Furthermore, the present invention will be described with respect to a "third generation" CT system. However, the present invention is also applicable with second or fourth generation CT systems. Additionally, the present invention will be described with respect to the detection and conversion of x-rays, but one skilled in the art will readily appreciate that the present invention is also applicable with the detection and conversion of other high frequency electromagnetic energy including gamma rays.

Figure 1:
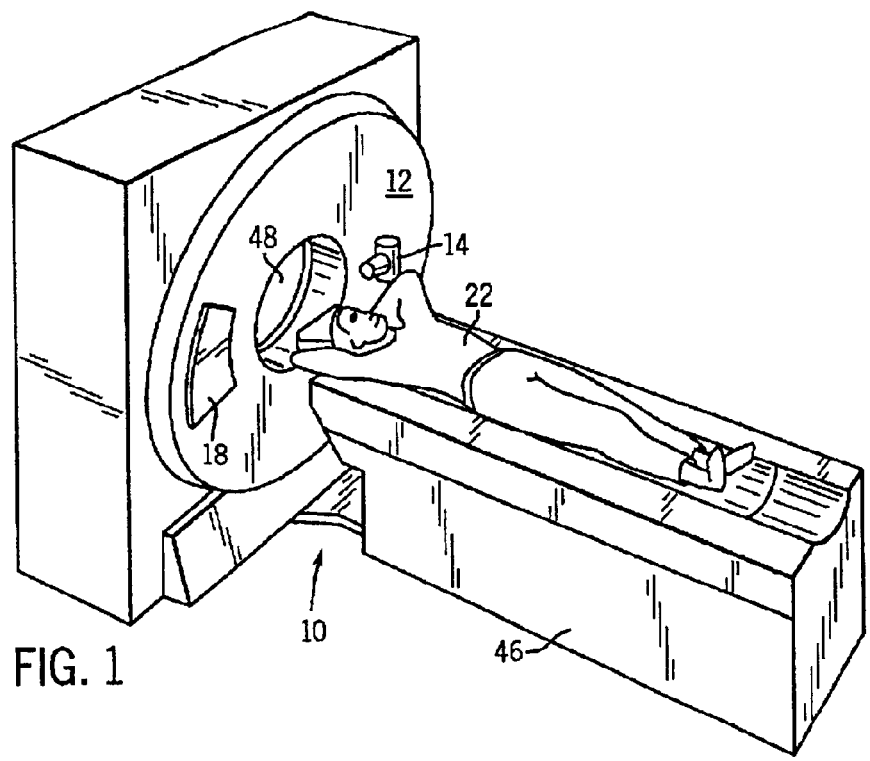
FIG. 1 is a perspective view of a CT imaging system incorporating the present invention.
Figure 2:
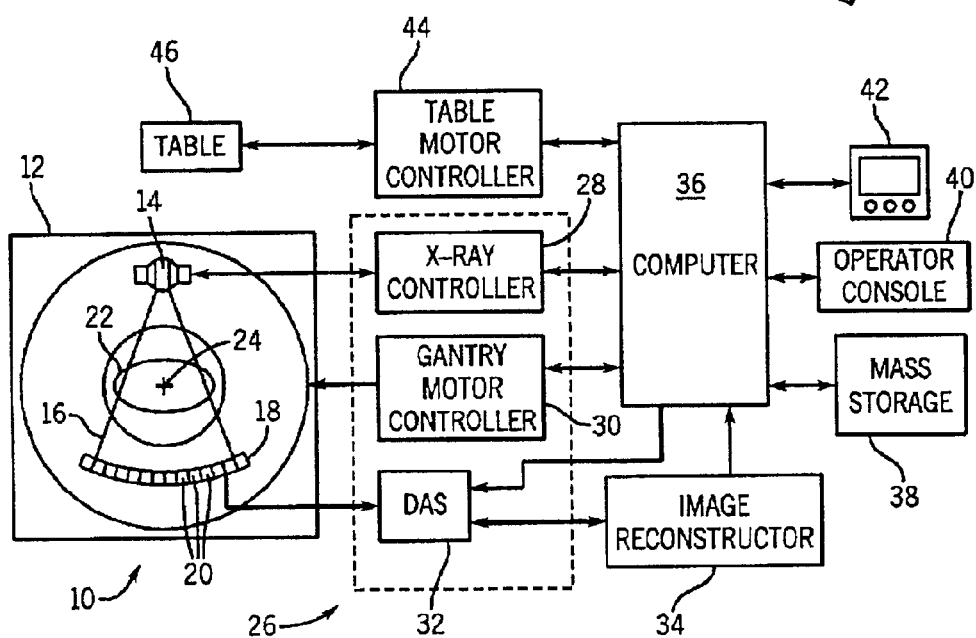
FIG. 2 is a perspective block schematic diagram of the system illustrated in FIG. 1.

Referring to FIGS. 1 and 2, an exemplary computed tomography (CT) imaging system 10 is shown as including a gantry 12 representative of a "third generation" CT scanner. Gantry 12 has an x-ray source 14 that projects a beam of x-rays 16 toward a detector array 18 on the opposite side of the gantry 12. Detector array 18 is formed by a plurality of detectors 20 which together sense the projected x-rays that pass through a medical patient 22. Each detector 20 produces an electrical signal that represents the intensity of an impinging x-ray beam and hence the attenuated beam as it passes through the patient 22. During a scan to acquire x-ray projection data, gantry 12 and the components mounted thereon rotate about a center of rotation 24. Detector array 18 and detectors 20 can be any number of high frequency electromagnetic energy detectors, such as gas-filled, scintillation cell-photodiode, and semiconductor detectors as is know to those skilled in the art of detector design.

Rotation of gantry 12 and the operation of x-ray source 14 are governed by a control mechanism 26 of CT system 10. Control mechanism 26 includes an x-ray controller 28 that provides power and timing signals to an x-ray source 14 and a gantry motor controller 30 that controls the rotational speed and position of gantry 12. A data acquisition system (DAS) 32 in control mechanism 26 samples analog data from detectors 20 and converts the data to digital signals for subsequent processing. An image reconstructor 34 receives sampled and digitized x-ray data from DAS 32 and performs high-speed reconstruction. The reconstructed image is applied as an input to a computer 36 which stores the image in a mass storage device 38.

Computer 36 also receives commands and scanning parameters, such as patient size and task dependency, from an operator via console 40 that has a keyboard for entering commands and scanning parameters. An associated cathode ray tube display 42 allows the operator to observe the reconstructed image and other data from computer 36. The operator supplied commands and parameters are used by computer 36 to provide control signals and information to DAS 32, x-ray controller 28 and gantry motor controller 30. In addition, computer 36 operates a table speed controller 44 which controls a variable speed table 46 during imaging of a patient 22 within gantry 12. Particularly, table 46 is configured to move a patient 22 through a gantry opening 48 along an axis 50, and may include a single or multiple speed settings.

In operation, a scan subject such as a medical patient 22 is positioned within the CT scanner or imaging device 10 on variable speed table 46 with a selected region of the patient chosen for scanning adjacent to the gantry 12. A technician or health-care operator inputs data into the operator console 40, thereby defining a region-of interest (ROI) such as a cardiac region. The computer 36 then instructs the table speed controller 44 to move the table 46 towards the gantry opening 48 causing the patient 22 to enter the gantry opening 48. Control mechanism 26 causes x-ray controller 28 to provide power and timing signals to x-ray source 14 while the gantry motor controller 30 causes rotation of gantry 12 to acquire imaging data of the patient 22 passing through the gantry 12. Data acquired is then transmitted to DAS 32 in the form of electrical signals and image reconstructor 34 for digitalization and subsequent image reconstruction. Computer 36 then processes the digitized x-ray data to provide a reconstructed image of the ROI on display 42.

Figure 3:
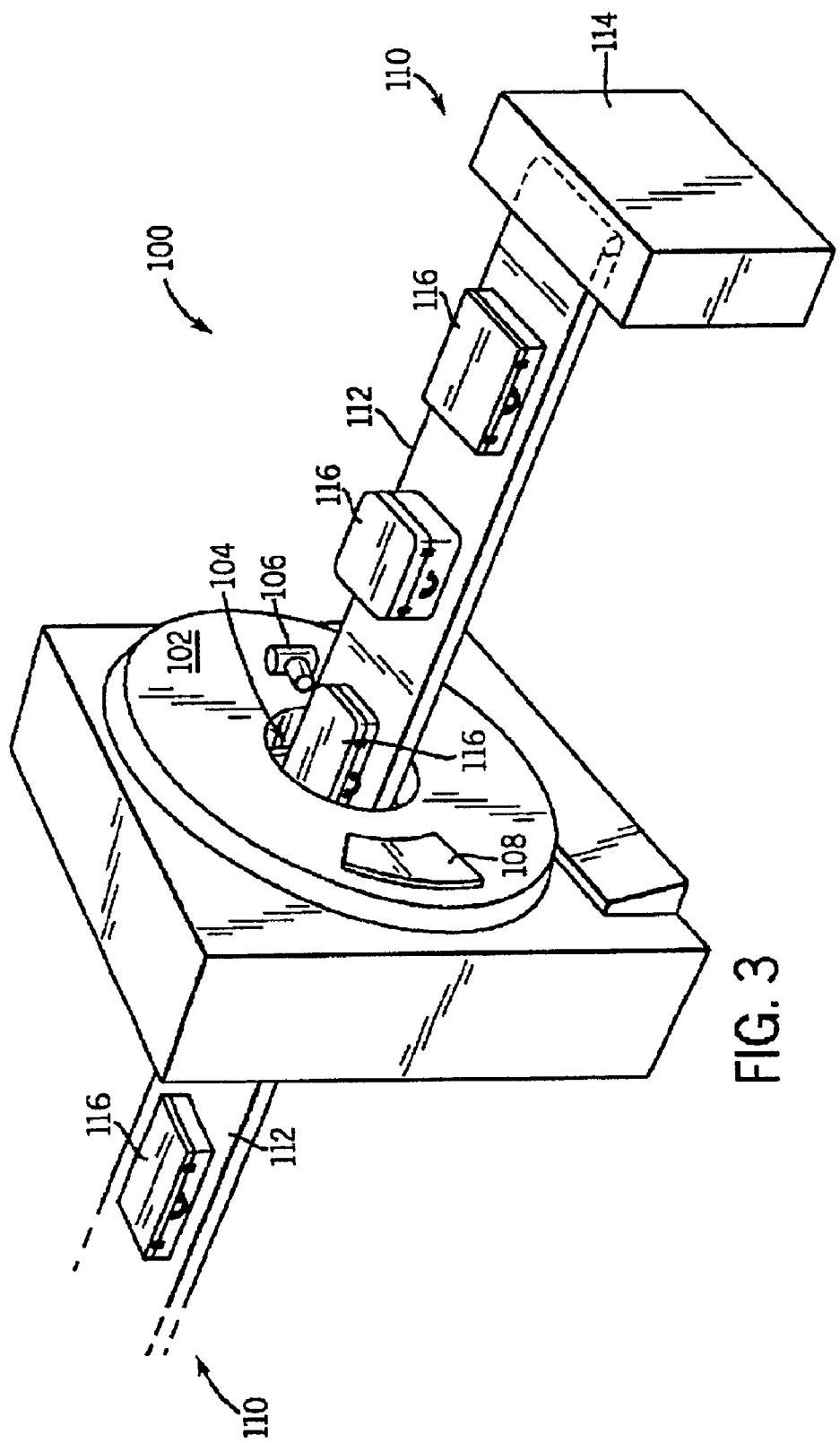
FIG. 3 is a pictorial view of a CT system for use with a non-invasive package inspection system.

Referring now to FIG. 3 and in accordance with an alternate embodiment of the present invention, a non-invasive package/baggage inspection system 100 includes a rotatable gantry 102 having an opening 104 therein through which packages or pieces of baggage may pass. The rotatable gantry 102 houses a high frequency electromagnetic energy source 106 as well as a detector assembly 108. A conveyor system 110 is also provided and includes a conveyor belt 112 supported by structure 114 to automatically and continuously pass packages or baggage pieces 116 through opening 104 to be scanned. Objects 116 are fed through opening 104 by conveyor belt 112, imaging data is then acquired, and the conveyor belt 112 removes the packages 116 from opening 104 in a controlled and continuous manner. As a result, postal inspectors, baggage handlers, and other security personnel may non-invasively inspect the contents of packages 116 for explosives, knives, guns, contraband, etc.

Figure 4:
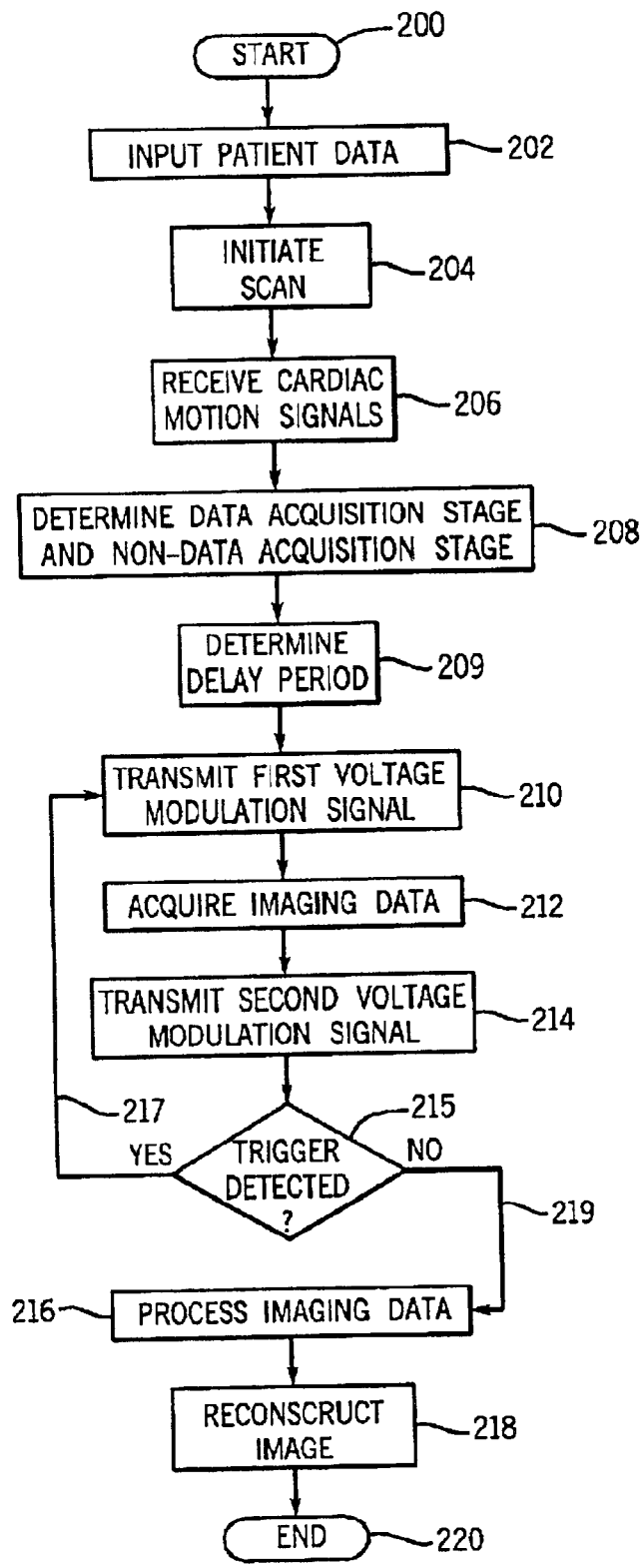
FIG. 4 is a flow chart showing a process in accordance with one embodiment of the present invention.

Referring to FIG. 4, a flow chart illustrating the steps and acts associated with an algorithm in accordance with the present invention is shown. The algorithm is initiated at 200 by a technician or CT scanner operator who provides input to the computer at 202 related to patient data such as sex, weight, and size. Generally, such operator-entered input includes a starting position and an ending position. A scan is initiated at 204 which causes the patient to enter opening 48 of FIG. 1. Simultaneously therewith, a set of EKG signals are acquired at 206 from a set of EKG electrodes (not shown) affixed to a torso region of the patient. The EKG signals detect motion signals including diastolic and systolic phases of the cardiac region of the patient. The EKG signals are acquired at 206 and transmitted to controller 26 or computer 36 for analysis.

Upon reception of EKG signals at 206, a primary data acquisition stage and a secondary or non-data acquisition stage are determined at 208. The stages are determined from trigger pulses found in the set of EKG signals. A period of delay after each triggered pulse is then determined at 209. A voltage modulation signal is then transmitted at 210 to the x-ray controller 28, FIG. 2, to cause a first voltage be applied to the x-ray source. That is, the x-ray source is energized to an "ON" state. The ON state is maintained for sufficient time to acquire imaging data at 212. After the imaging data is acquired for that data acquisition stage, a modulation signal is transmitted at 214 to the x-ray controller to energize the x-ray source to a second voltage. The second voltage corresponds to an "OFF" state thereby reducing x-ray emissions to the patient. In one embodiment, the second voltage is a zero voltage.

The second voltage is maintained until another trigger in the set of EKG signals is detected at 215. If a trigger is detected 217, the algorithm returns to step 210 with the transmission of the first voltage signal to drive the x-ray source to a relative maximum voltage. If no other triggers are detected 219, the algorithm continues to data processing at 216 for subsequent image reconstruction at 218. The algorithm then ends at 220.

Preferably, during the secondary or non-data acquisition stage a spectral filter (not shown) is used to filter out any lower energy x-rays from the high frequency electromagnetic energy beam. Further, a bowtie filter may also be implemented to reduce the range of intensity values received by the detector to also lower patient x-ray exposure during the secondary or non-data acquisition stage.

The EKG signals acquired from the patient are used to establish an imaging profile for the acquisition of imaging data. Pursuant to the imaging profile, the x-ray source is variably energized to modulate the projection of x-rays toward the patient. Modulating the voltage applied to the x-ray source allows for reduction of radiation exposure to the patient during the secondary or non-data acquired stages by limiting x-ray emissions without allowing the filament of the x-ray tube to cool beyond an acceptable level.

While EKG signals have heretofore been described as a means of developing an imaging profile, other data signals may be acquired and analyzed to develop an imaging profile including respiratory data signals.

Figure 5:
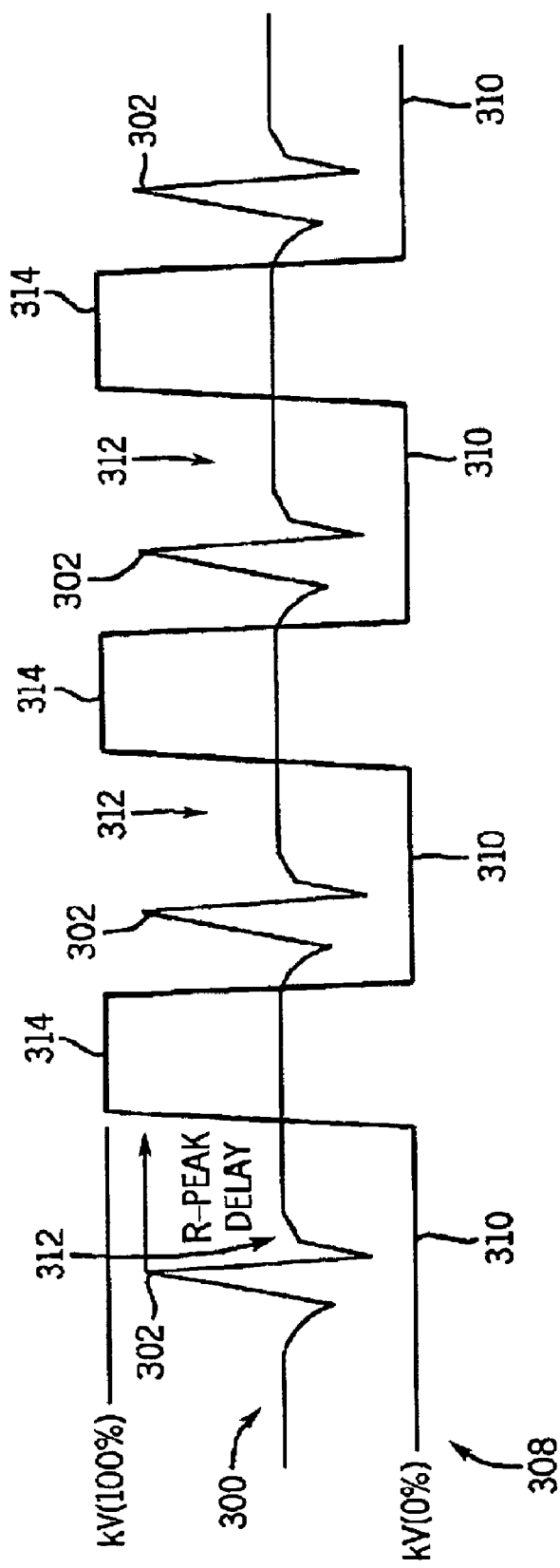
FIG. 5 is a representative cardiac data signal and a voltage modulation signal superimposed thereon to illustrate application of that set forth in FIG. 4.

Referring now to FIG. 5, the present invention will be described schematically with respect to a cardiac motion signal and a voltage modulation signal. As described previously, a cardiac motion signal 300 is detected from a plurality of EKG sensors affixed to a torso region of the scan subject. The EKG signal 300 corresponds to the systolic and diastolic phases of the scan subject's cardiac phases. Signal 300 includes a number of triggering pulses 302 that correspond to the beginning of each diastolic-systolic phase combination. That is, between successive triggering pulses 302, includes a single diastolic phase and a single systolic phase.

Also shown in FIG. 5 superimposed over EKG signal 300 is a voltage modulation signal 308 corresponding to the voltage applied to the x-ray tube of the imaging system. Voltage signal 308 is shown as superimposed over EKG signal 300 to illustrate the modulation of tube voltage with respect to the triggering pulses 302 of EKG signal 300. The highs and lows of the voltage signal 308 do not correspond to any particular voltage but illustrate a maximum and minimum voltage as a function of total voltage. As shown, tube voltage remains at a general minimum 310 until after a triggering pulse 302 followed by a predetermined delay 312. After the delay 312, the voltage as indicated by voltage signal 308 is driven to a relative maximum 314. The relative maximum voltage 314 is maintained until sufficient data is acquired for image reconstruction. That is, the relative maximum voltage 314 energizes the x-ray project source or tube to emit x-rays toward the scan subject for subsequent data acquisition. Once sufficient data has been acquired for image reconstruction, the tube voltage returns to a relative minimum 310 thereby reducing the x-ray emissions of the x-ray projection source until the tube voltage is once again driven to a relative maximum. As shown, the tube voltage will be driven to the relative maximum when a second triggering pulse 302 is detected and the requisite period of delay 312 has passed.

The present invention has been described with respect to the acquisition of imaging data using EKG signals to modulate tube voltage during the data acquisition to reduce x-ray emissions to the scan subject. The EKG signals are analyzed to determine an imaging profile and pursuant to that imaging profile a primary data acquisition stage and a secondary or non-data acquisition stage are determined. The primary data acquisition stage corresponds to a high voltage being applied to the projection source and the secondary or non-data acquisition stage corresponds to a lower voltage being applied to the x-ray projection source. Preferably, zero voltage is provided to the x-ray projection source during the non-data acquisition stage.

Therefore, in accordance with one embodiment of the present invention, a method of voltage modulation for computed tomography (CT) imaging is provided. The method includes the steps of acquiring a set of EKG signals having a plurality of triggering pulses and determining a period of delay after each triggering pulse. The method further includes the step of energizing a high frequency electromagnetic energy source to a first voltage after each period of delay and acquiring a set of imaging data of a scan subject while the high frequency electromagnetic energy source is energized to the first voltage. After acquiring a set of imaging data, the high frequency electromagnetic energy source is then energized to a second voltage until a period of delay after a next triggering pulse.

In accordance with another embodiment of the present invention, a radiation emitting imaging system includes a high frequency electromagnetic energy projection source configured to project high frequency energy toward a scan subject. The system also includes a detector assembly configured to receive high frequency electromagnetic energy attenuated by the scan subject and output a plurality of electrical signals indicative of the attenuation to a data acquisition system. The system further includes a control configured to determine a plurality of primary data acquisition stages and a plurality of secondary or non-data acquisition stages. The control is further configured to energize the high frequency electromagnetic energy projection source to a first voltage during each primary data acquisition stage to acquire imaging data. The control is also configured to energize the high frequency electromagnetic energy projection source to a second voltage during each secondary or non-data acquisition stage. The control is also configured to reconstruct an image of a scan subject from the imaging data acquired during each data acquisition stage.

In accordance with a further embodiment of the present invention, a computer readable storage medium having a computer program stored thereon and representing a set of instructions is provided. The set of instructions when executed by a computer causes the computer to analyze a set of cardiac motion signals acquired from a set of sensors affixed to a torso region of a scan subject. The set of instructions further causes the computer to determine from the set of cardiac motion signals a number of data acquisition stages and a number of non-data acquisition stages. The computer is then caused to transmit a first voltage modulation signal to a voltage source configured to energize an x-ray projection source used to project x-rays to the scan subject for data acquisition. The first voltage modulation signal is configured to drive the voltage source to the first voltage during each primary data acquisition stage. The computer is then caused to acquire a set of imaging data. Thereafter, the computer is caused to transmit a second voltage modulation signal to the voltage source wherein the second voltage modulation signal is configured to drive the voltage source to a second voltage for each secondary or non-data acquisition stage.

The present invention has been described in terms of the preferred embodiment, and it is recognized that equivalents, alternatives, and modifications, aside from those expressly stated, are possible and within the scope of the appending claims.

What is claimed is:

1. A method of voltage modulation for computed tomography (CT) imaging comprising the steps of:
    acquiring a set of cardiac signals having a plurality of triggering pulses;
    determining a period of delay after each triggering pulse;
    after each period of delay, energizing a high frequency electromagnetic energy source to a data acquisition voltage;
    acquiring a set of imaging data of a scan subject; and
    after acquiring the set of imaging data, energizing the high frequency electromagnetic energy source to a non-data acquisition voltage until the period of delay after a next triggering pulse.

2. The method of claim 1 wherein the non-data acquisition voltage is less than the data acquisition voltage.

3. The method of claim 1 further comprising the steps of:
    determining a primary and a secondary imaging stage from the set of cardiac signals;
    energizing the high frequency electromagnetic energy projection source to the data acquisition during the primary imaging stage; and
    energizing the high frequency electromagnetic energy projection source to the non-data acquisition voltage during the secondary imaging stage.

4. The method of claim 3 further comprising the step of filtering low energy high frequency electromagnetic energy projected to the scan subject to reduce high frequency electromagnetic energy exposure to the scan subject.

5. The method of claim 1 further comprising the step of determining a radiation dosage profile from the set of cardiac signals.

6. A radiation emitting imaging system comprising:
    a high frequency electromagnetic energy projection source configured to project high frequency energy toward a scan subject;
    a detector assembly to receive high frequency electromagnetic energy attenuated by the scan subject and output a plurality of electrical signals indicative of the attenuation to a data acquisition system (DAS);
    a control configured to:
        determine a primary data acquisition stage and a secondary data acquisition stage for an R-R interval, the primary data acquisition stage beginning after a triggering pulse and the secondary data acquisition stage occurring after the primary data acquisition stage and ending before a next triggering pulse of a next R-R interval;
        energize the high frequency electromagnetic energy projection source to a first voltage during the primary data acquisition stage to acquire primary imaging data;
        energize the high frequency electromagnetic energy projection source to a second voltage different from the first voltage during the secondary data acquisition stage to acquire secondary imaging data; and
        reconstruct an image of the scan subject from imaging data acquired during each data acquisition stage.

7. The system of claim 6 further comprising a bowtie filter configured to filter a portion of the nigh frequency electromagnetic energy projected by the high frequency electromagnetic energy projection source to the scan subject.

8. The system of claim 6 further comprising a plurality of EKG sensors configured to acquire a set of EKG signals of a cardiac region of the scan subject.

9. The system of claim 8 wherein the control is further configured to determine the primary data acquisition stage and the secondary data acquisition stage from the set of EKG signals.

10. The system of claim 9 wherein the control is further comprised to determine a number of subsets from the set of EKG signals and determine a triggering pulse within each subset and energize the high frequency electromagnetic energy projection source to the first voltage after a delay of the triggering pulse.

11. A computer readable storage medium having a computer program stored thereon and representing a set of instructions that when executed by a computer causes the computer to:
    analyze a set of cardiac motion signals acquired from a set of EKG sensors from a torso region of a scan subject;
    determine from the set of cardiac motion signals a number of primary data acquisition stages and a number of secondary acquisition stages, wherein each secondary acquisition stage follows a primary data acquisition stage and wherein each primary data acquisition stage occurs entirely within a respective single R—R interval;
    transmit a first voltage modulation signal to a voltage source configured to energize an x-ray projection source used to project x-rays to the scan subject for data acquisition, the first voltage modulation signal configured to energize the voltage source to a first voltage for each primary data acquisition stage;
    acquire a set of imaging data; and
    transmit a second voltage modulation signal to the voltage source, the second voltage modulation signal being configured to energize the voltage source to a second voltage for each secondary acquisition stage, the second voltage being less than the first voltage.

12. The computer readable storage medium of claim 11 wherein the set of instructions further causes the computer to determine a dosage profile from the set of EKG signals and modulate the voltage source according to the dosage profile.

13. The computer readable storage medium of claim 11 wherein the set of instructions further causes the computer to reduce x-ray projections to the scan subject during the number of secondary acquisition stages.

14. The computer readable storage medium of claim 11 wherein the set of instructions further causes the computer to determine the first voltage from a set of imaging parameters on a per imaging session basis.

15. The computer readable storage medium of claim 11 wherein the number of secondary acquisition states includes a number of non-data acquisition stages.

16. A method of cardiac CT imaging comprising the steps of:
   acquiring a series of cardiac signals defining a number of cardiac cycles each cardiac cycle defined by successive R pulses;
   determining a primely acquisition period that begins after a first R pulse of a cardiac cycle and a secondary acquisition period that occurs after the primary acquisition period and begins before a second R pulse of the cardiac cycle for the number of cardiac cycles;
   energizing an x-ray source to a default, non-zero voltage;
   initiating CT data acquisition for the number of cardiac cycles;
   energizing the x-ray source to a primary voltage that exceeds the default, non-zero voltage during CT data acquisition for the primary acquisition period; and
   returning the x-ray source to the default, non-zero voltage during CT data acquisition for the secondary acquisition period.

17. The method of claim 16 wherein the primary voltage includes a maximum voltage.

18. A radiation emitting imaging system comprising:
   a high frequency electromagnetic energy projection source configured to project high frequency energy toward a scan subject;
   a detector assembly to receive high frequency electromagnetic energy attenuated by the scan subject and output a plurality of electrical signals indicative of the attenuation to a data acquisition system (DAS);
   a control configured to:
      model data acquisition for a heart of the scan subject based on a series of cardiac signals defining a number of cardiac cycles of the heart, each cardiac cycle defined by a first R pulse end a second R pulse:
      apply a first voltage to the high frequency electromagnetic energy projection source between the first and the second R pulses of each cardiac cycle;
      acquire imaging data of the heart with the high frequency electromagnetic energy projection source at the first voltage;
      thereafter apply a second voltage to the high frequency electromagnetic energy projection source, wherein said application of the second voltage occurs before the second R pulse of a current cardiac cycle, the first voltage exceeding the second voltage; and
   reconstruct an image of the scan subject for multiple phases of each cardiac cycle.

19. The system of claim 18 wherein the second voltage includes a default voltage and the first voltage includes a maximum voltage.

20. The system of claim 19 wherein the default voltage includes a minimum voltage required to acquire data.

* * * * *

UNITED STATES PATENT AND TRADEMARK OFFICE
CERTIFICATE OF CORRECTION

PATENT NO. : 6,836,529 B2
DATED : December 28, 2004
INVENTOR(S) : Li et al.

It is certified that error appears in the above-identified patent and that said Letters Patent is hereby corrected as shown below:

Column 7,
Line 46, insert the word -- voltage -- after the word "acquisition";

Column 10,
Line 13, delete "end" and substitute therefor -- and --.

Signed and Sealed this

Twenty-second Day of March, 2005

JON W. DUDAS
*Director of the United States Patent and Trademark Office*